United States Patent [19]

Boettcher et al.

[11] Patent Number: 5,292,915

[45] Date of Patent: Mar. 8, 1994

[54] COMPOUNDS CONTAINING CARBONATE GROUPS AND CARBONYL GROUPS AND THE PREPARATION AND USE THEREOF

[75] Inventors: Andreas Boettcher, Nussloch; Manfred Schwartz, Ludwigshafen, both of Fed. Rep. of Germany

[73] Assignee: BASF Aktiengesellschaft, Ludwigshafen, Fed. Rep. of Germany

[21] Appl. No.: 830,854

[22] Filed: Feb. 4, 1992

[30] Foreign Application Priority Data

Feb. 21, 1991 [DE] Fed. Rep. of Germany ....... 4105355

[51] Int. Cl.$^5$ ........................ C07C 69/96; C07F 5/04
[52] U.S. Cl. ........................... 558/273; 554/85; 554/88; 554/90; 554/91; 554/92; 554/94; 554/95; 554/101; 554/102; 554/105; 554/106; 554/107; 554/108; 554/109; 554/110; 554/112; 554/113; 554/116; 554/117; 554/118; 554/119; 554/120; 554/121; 554/122; 558/265; 558/268; 558/269; 558/270; 558/271; 558/272
[58] Field of Search ............... 558/273, 265, 268, 269, 558/270, 271, 272; 554/116, 85, 88, 90, 91, 92, 94, 95, 101, 102, 105, 106, 107, 108, 109, 110, 112, 113, 116, 117, 118, 119, 120, 121, 122

[56] References Cited

U.S. PATENT DOCUMENTS 4,199,420   4/1980   Photis ................................ 558/273
4,602,097   7/1986   Curtis ................................ 558/273

FOREIGN PATENT DOCUMENTS 0108037   5/1984   European Pat. Off. .
0377191   7/1990   European Pat. Off. .
2619831  11/1977   Fed. Rep. of Germany .
59-20313   5/1984   Japan .
2100722    1/1983   United Kingdom .

OTHER PUBLICATIONS

New Polymeric Mat., vol. 1, No. 1, 1987, pp. 63–83, C. Carlini, et al., "Polymeric Photoinitiators Containing Side Chain Benzophenone Chromophores: Relationships Between Structure and Activity".

Primary Examiner—Johann Richter
Attorney, Agent, or Firm—Oblon, Spivak, McClelland, Maier & Neustadt

[57] ABSTRACT

The invention relates to compounds containing carbonate groups and carbonyl groups and having the general formula $$R-\overset{O}{\underset{\|}{C}}-R^1$$

in which
R stands for a $C_1$–$C_4$-alkyl radical, an aryl radical, or a radical $R^1$, where
$R^1$ has the following formula <chemical structure: benzene ring with substituents R$^2$, R$^3$, R$^4$, R$^5$, R$^6$> in which
$R^2$ to $R^6$ stand for H, alkyl, OH, O-alkyl, SH, S-alkyl, halogen, N(alkyl)$_2$, or N(alkyl)(aryl) and at least one but not more than three of the radicals $R^2$ to $R^6$ stand for a radical of the formula $$-O-\underset{\underset{O}{\|}}{C}-O-A_k-B_l-C_q-O-Z$$

in which
A, B and C stand for alkylene, cycloalkylene, oxaalkylene, polyoxaalkylene or arylene, k and l both stand for an integer from 1 to 80, and the end group Z stands for alkyl, aryl, alkoxycarbonyl, alkoxycarbonyloxy, or aryl.

These compounds are suitable for use as emulsifiers for dispersions.

3 Claims, No Drawings

COMPOUNDS CONTAINING CARBONATE GROUPS AND CARBONYL GROUPS AND THE PREPARATION AND USE THEREOF

The invention relates to compounds containing carbonate groups and carbonyl groups, to a process for the preparation thereof and to their use as radiosensitive emulsifiers for dispersions.

Acetophenones and benzophenones sensitive to UV radiation are frequently used as photoinitiators in radiocurable dispersions for lacquers and coating compositions.

U.S. Pat. No. 4,602,097 reveals compounds of the following formulae:

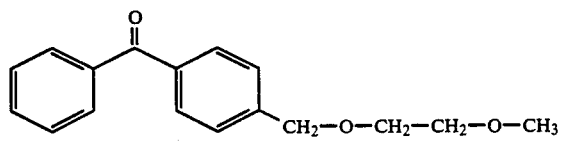

(cf. US-A 4,199,420),

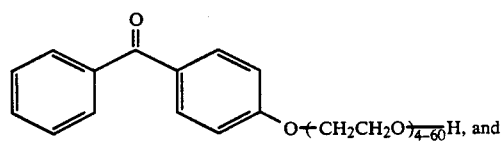

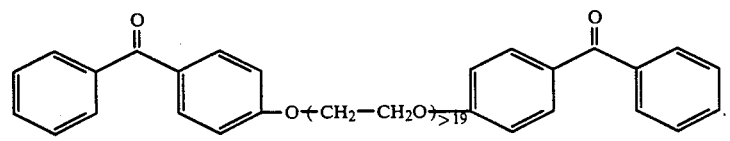

In the case of "Uvecryl ®P36", a commercial product of UCB, a particularly long spacer consisting of four oxyethylene units separates the benzophenone from the acryloxy radical:

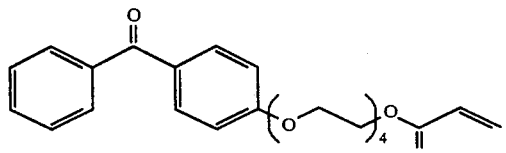

This compound is described, for example, in UCB's Technical Bulletin 2480/885 (1985) or in New Polym. Mat. 1, 63 (1987) and can be used in photopolymers for coating compositions.

Further examples of suitable compounds of this kind are described in EP-A 108,037, JP 5-90 20,313 and GB-PS 2,100,722.

All of the compounds described are either non-dispersible with monomers complying with present-day technical standards or show poor photochemical activity.

It is an object of the present invention to provide compounds containing carbonate groups and carbonyl groups and a process for the preparation thereof, which compounds are suitable for use as radiosensitive emulsifiers for dispersions.

We have found that the dispersibility and photochemical activity are surprisingly considerably increased when a carbonate group links the initiator moiety, acting as chromophore, to the polyoxaalkylene radical.

The present invention relates to a compound containing carbonate groups and carbonyl groups and having the general formula (I)

in which

R stands for a straight-chain $C_1$-$C_4$-alkyl radical, for a branched-chain $C_3$-$C_4$-alkyl radical, optionally substituted, for a $C_6$-$C_{20}$-aryl radical, or for a radical $R^1$, where $R^1$ has the following formula

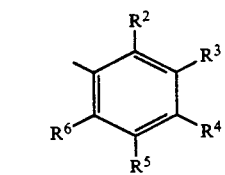

in which $R^2$ to $R^6$ are the same or different and can stand for H, $C_1$-$C_4$-alkyl, such as methyl, ethyl, isopropyl, and butyl, or for phenyl, OH, $OCH_3$, $OC_2H_5$, SH, $SCH_3$, $SC_2H_5$, $SO_3H$, $SO_3^\ominus$, F, Cl, Br, CN, COOH, $COO^\ominus$, COO-($C_1$- $C_{17}$-alkyl), COO-aryl, $CF_3$, N($C_1$- $C_4$-alkyl)$_2$, N($C_1$- $C_4$-alkyl)($C_6$- $C_{20}$-aryl), or N($C_6$- $C_{20}$-aryl)$_2$, for example phenyl, tosyl, xylyl, and naphthyl, provided that $R^2$ and $R^6$ do not stand for OH, SH, or primary or secondary alkyl and at least one but not more than three of the radicals $R^2$ to $R^6$ stand for a radical of the formula

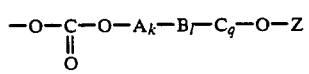

in which

A, B and C may be the same or different and each can stand for a radical of the formula

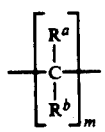

in which
m is an integer from 1 to 6 and
$R^a$ and $R^b$ are the same or different and can denote H, OH, aryl, COOH, COOCH$_3$, COOC$_2$H$_5$, SO$_3$H, or C$_1$-C$_4$-alkyl,
for a divalent oxaalkylene radical of the formula

where y is an integer from 1 to 80 and $R^a$ and $R^b$ have the meanings stated,
for a radical of the formula

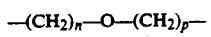

where n is an integer from 1 to 5 and p is an integer from 1 to 5,
for a polyoxaalkylene radical of from 2 to 20 oxygen atoms linked by at least one —CH$_2$— or —CH$_2$—CH(CH$_3$)-group,
for a radical of the formula

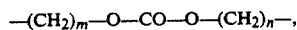

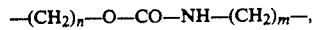

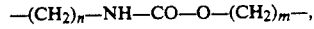

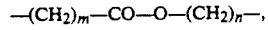

or

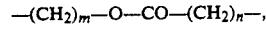

where m is an integer from 1 to 10 and n is an integer from 1 to 10,
for a C$_5$-C$_{10}$-cycloalkylene radical, optionally substituted, a (bis)methylenecycloalkylene radical of from 6 to 12 carbon atoms or an o-, m- or p-phenylene radical, optionally substituted, and
k, l and q are each an integer from 1 to 80, and
$A_k$ and $C_q$ can alternatively be single bonds and at least one of the radicals $A_k$, $B_l$ and $C_q$ contains two oxygen atoms, and
Z stands for H, C$_1$-C$_6$-alkyl (e.g. isopropyl or t-butyl), phenyl, phenyl substituted by straight-chain or branched-chain C$_1$-C$_{20}$-alkyl, or a radical of the formula

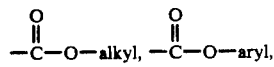

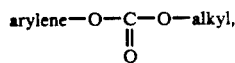

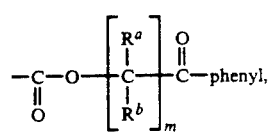

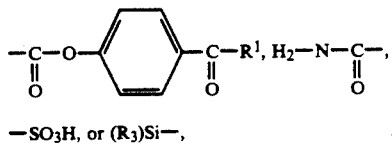

—SO$_3$H, or (R$_3$)Si—, or when R denotes an aryl radical, one of the radicals $R^2$ to $R^6$ can stand for a sulfur atom which links the aryl radical to $R^1$ in its ortho-position.

Surprisingly, the compounds of the invention exhibit very high photochemical activity under short-wave to medium-wave UV radiation (254–400 nm), good stability on storage and excellent dispersibility.

The invention also relates to a process for the preparation of a compound of the general formula (I), wherein a compound of the general formula (II)

$$G-\overset{O}{\overset{\|}{C}}-O-A_k-B_l-C_q-O-Z, \quad (II)$$

in which
A, B, C, k, l, q, and Z have the meanings stated in claim 1, and
G stands for a group selected from tosylate, C$_1$-C$_5$-alkoxy, halogen, such as chlorine or bromine, imidazolyl, pyrazolyl, and phosphonium, sulfonium, ammonium and pyridinium cations,
is reacted with a compound of the general formula (IIIa)

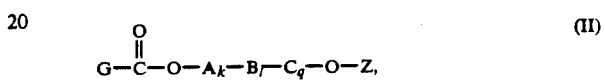

in which
$R^2$ to $R^6$ have the meanings stated above and
$R^7$ stands for a straight-chain C$_1$-C$_4$-alkyl radical, preferably methyl, ethyl, or n-propyl, for a branched-chain C$_3$-C$_4$-alkyl radical, optionally substituted, such as isopropyl, s-hydroxy-isopropyl, s-dimethylaminopropyl, s-morpholinopropyl, or t-butyl, or for a C$_6$-C$_{20}$-aryl radical, for example phenyl, tolyl or naphthyl,
provided that at least one of the radicals $R^2$ to $R^6$ stands for a hydroxyl group,
in an equimolar ratio or in a molar ratio of 2:1 or 3:1 depending on the number of hydroxyl groups in the radicals $R^2$ to $R^6$, optionally in the presence of an inert solvent or solvent mixture and a basic catalyst, at a temperature of from 0° to 100° C. under anhydrous conditions.

The present invention also relates to a process for the preparation of a compound of the general formula (I), wherein a compound of the general formula (IV)

$$HO-A_k-B_l-C_q-O-Z \quad (IV),$$

in which A, B, C, k, l, q and Z have the meanings stated in claim 1,
is reacted with a compound of the general formula (IIIb)

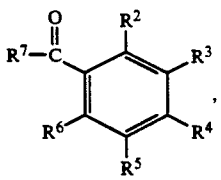
(IIIb)

in which
R² to R⁶ have the meanings stated in claim 1 and
R⁷ stands for a straight-chain $C_1$–$C_4$-alkyl radical, a branched-chain $C_3$–$C_4$-alkyl radical, optionally substituted, or a $C_6$–$C_{20}$-aryl radical,
provided that at least one of the radicals R² to R⁶ denotes a group of the formula

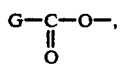

in which
G stands for tosylate, $C_1$–$C_5$-alkoxy, halogen, e.g. chlorine or bromine, or imidazolyl, pyrazolyl or a phosphonium, sulfonium, ammonium or pyridinium cation,
in an equimolar ratio or in a molar ratio of 2:1 or 3:1 depending on the number of groups of the formula

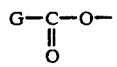

in the radicals R² to R⁶, optionally in the presence of an inert solvent or solvent mixture and a basic catalyst, at a temperature of from 0° to 100° C. under anhydrous conditions.

The compound of the general formula (II) used in the first-named process is preferably a chloroformate of an alkylphenol optionally chain-extended with ethylene oxide or a bischloroformate of an oxyalcohol derived from ethylene oxide and/or propylene oxide.

The compound of the general formula (IIIb) used in the second-named process is an optionally substituted chloroformylacetophenone, chloroformylbenzophenone, or chloroformylthioxanthone.

The process of the invention are advantageously carried out in the presence of at least an equimolar amount of a strong non-nucleophilic base, advantageously a tertiary amine, and at a temperature of from 20° to 60° C.

The processes of the invention are preferably carried out in an inert anhydrous solvent, if necessary with the exclusion of moisture.

The synthesis of aryl carbonates not containing copolymerizable end groups has been revealed (cf. JP-OS 59-001,438; JP-OS 59-170,033). A good overview is given by a) Houben-Weyl, Methoden der Organischen Chemie, Vol. 8, pp. 75, 101-107, Thieme-Verlag 1952, b) Kirk-Othmer, Encyclopedia of Chemical Technology, Vol. 4, pp. 758-771, John Wiley 1978, and c) Ullmann's Encyclopedia of Industrial Chemistry, Vol. A5, pp. 197-202, Verlag Chemie 1986.

The most important method of preparing carbonates comprises the reaction of chloroformates with alcohols. The procedure is described in detail in Houben-Weyl, Vol. 8 (see above) and in DE-PS 1,080,546 and J. Org. Chem. 26, 5119 (1961). The carbonates are formed in good to very good yields when the alcohol and the chloroformate are reacted in a molar ratio of 1:1 in the absence of solvent or in the presence of excess alcohol acting as solvent. In cases where the alcohol or phenol and/or chloroformate are present in the solid state, use will be made of aprotic solvents such as dichloromethane, dichloroethane, acetonitrile, toluene, xylene, etc.. It should be noted that the above citations refer exclusively to alcohols of not more than 10 carbon atoms.

The hydroxyacetophenones and hydroxybenzophenones required as starting materials are obtainable by known methods. For example, 4-hydroxybenzophenone is produced in a yield of approximately 90% by Friedel-Crafts acylation of phenol using benzoyl chloride in nitrobenzene in the presence of $AlCl_3$ or $TiCl_4$ (Houben-Weyl, 7/2a, p. 186) or free from isomers by oxidation of 4-hydroxy-diphenylmethane with 5,6-dichloro-2,3-dicyano-p-benzoquinone (Houben-Weyl 7/2a, p. 681).

Methods of synthesizing amino-substituted benzophenones such as 2-benzyl-2-(dimethylamino)-1-(4-hydroxyphenyl)butan-1-one or 1-(4-hydroxyphenyl)-2-methyl-2-morpholinopropan-1-one are described in EP-A 284,561 and EP-A 117,233.

2-Hydroxythioxanthone can be prepared from thiosalicylic acid and phenol by the method described in GB-PS 2,108,487 (1981) and GB-PS 2,108,979 (1982).

The aromatic chloroformates (cf. J. Prakt. Chem. 313, p.331, 1971 and loc. cit. 317, pp.62, 73, and 81, 1975) of the general formula (IIIb) can be prepared in good yields from a substituted phenol, e.g. 4-chloro-5'-fluoro-2'-hydroxybenzophenone, 4-chloro-4'-hydroxybenzophenone, 4,4'-dihydroxybenzophenone, 4-fluoro-4'-hydroxybenzophenone, 4-hydroxybenzophenone, 3-hydroxy-thioxanthone, (4-hydroxyphenyl)-2-hydroxy-2-propylketone (DE-OS 3,534,645) by phosgenation by standard methods disclosed in the literature using phosgene (e.g. Houben-Weyl, Methoden der Organischen Chemie, Vol. 8, Thieme-Verlag 1952), or trichloromethyl-chloroformate (diphosgene) (J. Prakt. Chem. 126, p.210, 1930, loc. cit. 128, p.233, 1930, Chem. Abstr. 95, p.81766, J. Org. Chem. 50, p.715, 1985, loc. cit. 41, p.2070, 1976, Angew. Chem. 89, p. 267, 1977), or crystalline triphosgene (Angew. Chem. 99, p.922, 1987), or N,N'-carbonyl-diimidazole or N,N'-carbonyl-di-s-triazole (Fieser 1, p.116, 1967).

Information on the use of alternative methods of phosgenation, e.g. reacting with chloroformates, is given in "Merck Kontakte" 1981 (1), pp. 14–18.

To synthesize the compounds of the invention it is necessary to use appropriately substituted mono- and di-alcohols. Examples of such compounds are:

Lutenso®AP 20 (=isononylphenol/ethylene oxide adduct containing, on average, 20 ethylene oxide units), Pluronic®PE 6400 (=ethylene oxide/propylene oxide block polymer, $\overline{M}_w$ approximately 2900).

Examples of chloroformates suitable for use as starting products are:

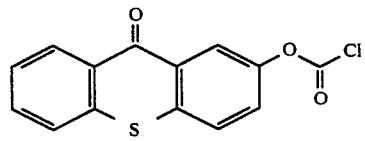

-continued

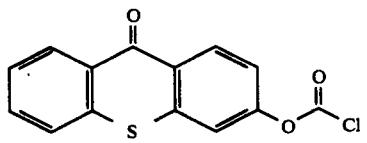
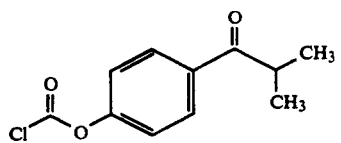
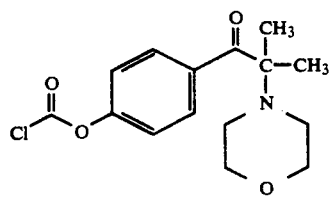
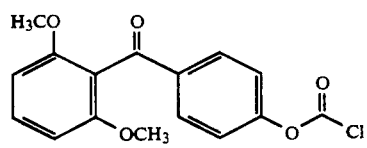
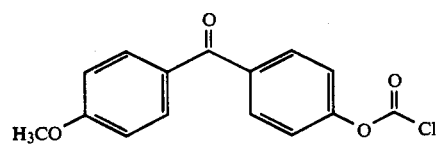
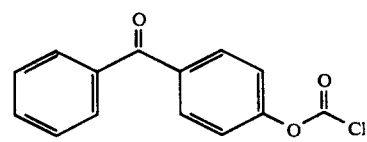
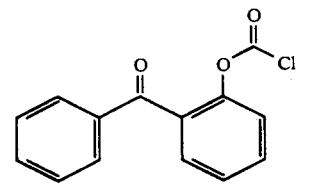
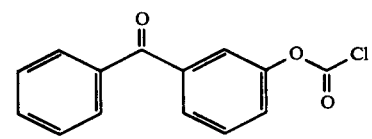
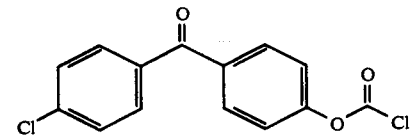
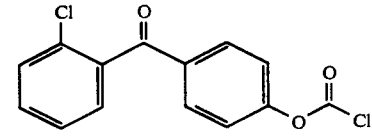

-continued

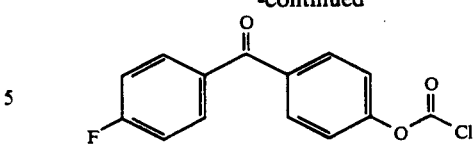
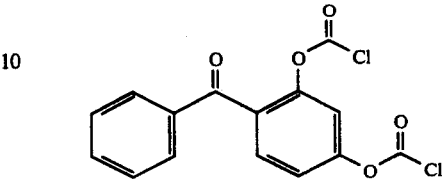
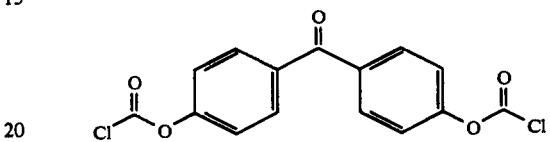
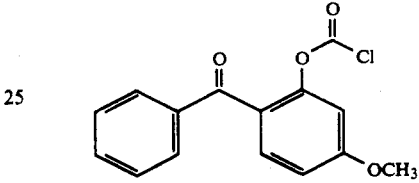

The reaction is carried out in an equimolar ratio (possibly with an excess of from 10% to 30) or in a molar ratio of 2:1 or 3:1 depending on the number of G—CO—O—groups in the radicals $R^8$ to $R^{12}$, with the exclusion of water and possibly in the presence of an inert solvent or solvent mixture and a basic catalyst, at a temperature of from 0° to 100° C. and preferably from 20° to 50° C.

For the conversion of the hydroxyacetophenones, hydroxybenzophenones or hydroxythioxanthones it will generally be necessary to use the corresponding chloroformates. These may be readily prepared in good yields using methods disclosed in the literature, for example in Eur. Polym. J.14, p.205 (1978); J. Polym. Sci. Polym. Symp. 66, p.41 (1979); and Bull. Soc. Chim. Belg. 93, p.159 (1984).

The acetophenone, benzophenone and thioxanthone derivatives of the invention have been found to be surprisingly easy to produce in good yields.

The manufacturing process will now be described in detail.

The chloroformates used for the reaction readily react with nucleophilic compounds, including water. For this reason, it is necessary to ensure that the reaction is carried out with the exclusion of all moisture by using dried non-nucleophilic solvents, such as acetonitrile, dichloromethane, dichloroethane, tetrahydrofuran, toluene, xylene, chlorobenzene, ethyl acetate, chloroform, etc. and, if necessary, to establish an inert gas atmosphere of, say, nitrogen, argon, or carbon dioxide.

Usually, the initial contents of the reactor will be a solution or suspension of the hydroxy compound in an inert solvent, which may be dispensed with if the starting compound is liquid at the reaction temperature, together with a basic non-nucleophilic amine, preferably triethylamine, 4-dimethylaminopyridine, imidazole, 1,4-diaza-bicyclo[2.2.2]octane, 1,5-diaza-bicyclo[4.3.0]-non-5-ene, 1,8-diaza-bicyclo[5.4.0]undec-7-ene, polyvinylpyridine, N,N'-dimethylpropylene urea, N,N'-dimethylethylene urea, etc., at a temperature of from 0° to 100° C. and preferably from 10° to 50° C. The chloroformyl compound, possibly dissolved in an inert solvent such as dichloromethane, dichloroethane, acetonitrile, toluene, chlorobenzene, xylene, etc., is then added dropwise with stirring at a temperature in the above range. This procedure is particularly suitable for relatively large batches.

Instead of said chloroformates, the following compounds may be similarly used for the synthesis process: tosylates, imidazolyl, pyrazolyl, and phosphonium, sulfonium, ammonium and pyridinium compounds.

Stirring is continued for from 1 to 48 hours, preferably from 1 to 20 hours, at a temperature of from 10° to 40° C., after which the product is isolated by the standard procedure of filtering, washing, and drying, followed by recrystallization, distillation, or extraction.

The acetophenones, benzophenones, and thioxanthones of the invention are suitable for use as radiocurable emulsifiers for aqueous polymer dispersions. They combine with the polymer particles preferentially at the surface thereof, where they are available for photolinking reactions (cf. German Patent Application P 41 05 354.0).

When our novel compounds containing carbonate and carbonyl groups involve —N< structures, it is advantageous to use them together with aromatic ketones such as benzophenone or acetophenone.

It may also be advantageous to use the novel compounds containing carbonate and carbonyl groups together with amines, preferably tertiary amines such as triethylamine, triethanolamine, or diethylethanolamine, in order to improve their radiosensitivity.

In the following Examples, the parts and percentages are by weight unless otherwise stated. The structure of all of the compounds named in the Examples was confirmed in some cases by independent synthesis experiments and in all cases by the correct $^1$H-NMR, IR, and mass spectra and by conforming elementary analysis results.

Examples of the synthesis of chloroformyl compounds suitable for use as starting materials:

1. 4-Chloroformylbenzophenone

A total of 3.4 kg of phosgene was passed through a solution of 4 kg of 4-hydroxybenzophenone and 190 g of benzyltrimethylammonium chloride in 11.4 kg of o-xylene over a period of 5 hours, during which time the internal temperature was raised from 95° to 120° C. The introduction of phosgene was then stopped, and stirring was continued for 30 minutes at 115° C. Before the product was worked up, the excess phosgene was expelled with nitrogen. The salt (catalyst) which precipitated toward the end of the reaction was filtered off, and the solvent was removed by distillation. There were obtained 4.9 kg (93%) of yellowish 4-chloroformylbenzophenone having a melting point of 67°–72° C. This crude product having a Cl content of 12.69% (theory=13.60%) was used unpurified as starting material for subsequent reactions.

The following chloroformyl compounds were prepared in a manner similar to that described under 1 above:

2. 2-Chloroformylthioxanthone

2-Hydroxythioxanthone was converted to 2-chloroformylthioxanthone (Cl content: found 12.03%, calc. 12.19%) in a yield of 79%.

3. 3-Chloroformylthioxanthone

3-Chloroformylthioxanthone was obtained in a yield of 63% from 3-hydroxythioxanthone (Cl content: found 11.22%, calc. 12.19%).

4. (4-Chloroformylphenyl)-(2-hydroxy-2-propyl)ketone (4-Hydroxyphenyl)-(2-hydroxy-2-propyl)ketone was converted to (4-chloroformylphenyl)-(2-hydroxy-2-propyl)ketone in a yield of 75% giving a crude product having a Cl content of 13.07% (calc. 14.61%).

5. 1-(4-Hydroxyphenyl)-2-methyl-2-morpholinopropan-1-one was first of all converted to the hydrochloride by phosgenation, and the latter was then converted to the free amine by carefully mixing it with 1,5-diazabicyclo[4.3.0]non-5-ene; yield 62% (Cl content: found 11.21%, calc. 11.37%).

Preparation of dispersion emulsifiers of the invention:

EXAMPLE 1

Reaction of 4-chloroformylbenzophenone with Lutensol ®AP 20

275 g (0.25 mole) of Lutensol ®AP 20 and 30 g (0.3 mole) of triethylamine were dissolved in 1000 ml of toluene at 25° C. 75 g (0.25 mole) of 4-chloroformylbenzophenone dissolved in 150 ml of toluene were then added dropwise over 30 minutes, and the mixture was then stirred for 15 hours at room temperature. The precipitated triethylamine hydrochloride was carefully isolated by filtration in vacuo, and the filtrate was concentrated to constant weight under oil pump vacuum.

Yield: 318 g (96%) of a colorless viscous liquid

The same product is obtained in a yield of 85% when 4-hydroxybenzophenone and phosgenated Lutensol-®AP 20 are reacted and worked up under the aforementioned conditions.

The following unsymmetrical carbonates were obtained in a manner similar to that described in Example 1.

EXAMPLES 2 to 10

| Example | Chloroformate | Lutensol ® | Yield |
|---|---|---|---|
| 2 | (structure A) | AP 6 | 87% |
| 3 | (structure A) | AP 10 | 92% |
| 4 | (structure B) | AP 6 | 95% |
| 5 | (structure B) | AP 10 | 94% |
| 6 | (structure B) | AP 20 | 97% |

-continued

| Example | Chloroformate | Lutensol ® | Yield |
|---|---|---|---|
| 7 |  | | |
| 8 | | AP 6 | 97% |
| 9 | 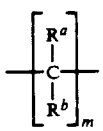 | AP 10 | 90% |
| 10 | | AP 20 | 87% |

EXAMPLE 11

Reaction of 4-chloroformylbenzophenone with Pluronic ® PE 6400

The initial contents of the reactor were 363 g (0.125 mole) of Pluronic ® PE 6400 and 30 g (0.3 mole) of triethylamine in 1000 ml of toluene at room temperature. To this there were added dropwise 75 g (0.25 mole) of 4-chloroformylbenzophenone dissolved in 150 ml of toluene, at 25° C. The reaction mixture was then stirred for 17 hours, cooled to about 10° C., carefully filtered, and concentrated to constant weight under oil pump vacuum.

Yield: 412 g (98%) of a clear, colorless, viscous liquid.

$^1$H-NMR, $^{13}$C-NMR, and IR spectra confirmed the following structure:

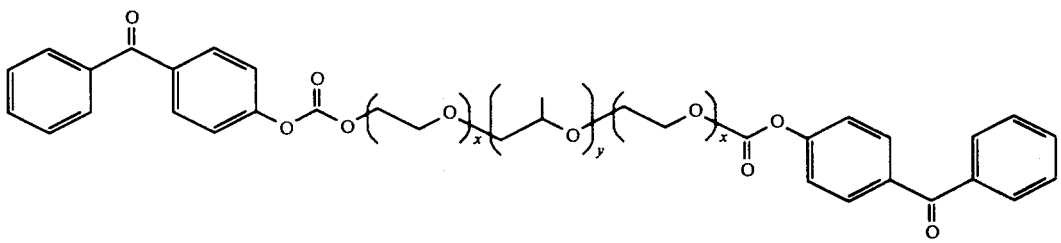

We claim:

1. A compound containing carbonate groups and carbonyl groups, and having the general formula (I)

$$R-\underset{\underset{O}{\|}}{C}-R^1 \quad (I)$$

in which

R is a straight-chain $C_1$–$C_4$-alkyl radical, a branched-chain $C_3$–$C_4$-alkyl radical optionally substituted, a $C_6$–$C_{20}$-aryl radical, or a radical $R^1$, where $R^1$ has the following formula

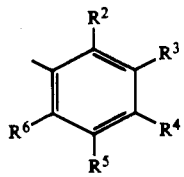

in which each of $R^2$ to $R^6$ is H, $C_1$–$C_4$-alkyl, phenyl, OH, $OCH_3$, $OC_2H_5$, SH, $SCH_3$, $SC_2H_5$, $SO_3H$, $SO_3^\ominus$, F, Cl, Br, CN, COOH, $COO^\ominus$, COO-($C_1$–$C_{17}$-alkyl), COO-aryl, $CF_3$, N($C_1$–$C_4$-alkyl)$_2$, N($C_1$–$C_4$-alkyl)($C_6$–$C_{20}$-aryl), or N($C_6$–$C_{20}$-aryl)$_2$, provided that $R^2$ and $R^6$ are not OH, SH, or primary or secondary alkyl and at least one but not more than three of the radicals $R^2$ to $R^6$ is a radical of the formula $$-O-\underset{\underset{O}{\|}}{C}-O-A_k-B_l-C_q-O-Z$$

in which each of A, B and C is a radical of the formula

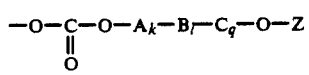

in which m is an integer from 1 to 6, and each of $R^a$ and $R^b$ is H, OH, aryl, COOH, $COOCH_3$, $COOC_2H_5$, $SO_3H$, or $C_1$–$C_4$-alkyl, a divalent oxaalkylene radical of the formula $$-(CHR^a-CHR^b-O)_y-$$

where y is an integer from 1 to 80 and $R^a$ and $R^b$ have the meanings stated, a radical of the formula $$-(CH_2)_n-O-(CH_2)_p-$$

where n is an integer from 1 to 5 and p is an integer from 1 to 5, a polyoxaalkylene radical of from 2 to 20 oxygen atoms linked by at least one $-CH_2-$ or $-CH_2-CH(CH_3)-$group, a radical of the formula $$-(CH_2)_m-O-CO-O-(CH_2)_n-,$$

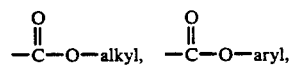

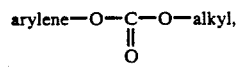

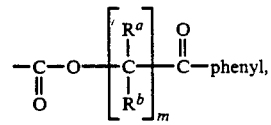

or

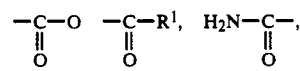

where m is an integer from 1 to 10 and n is an integer from 1 to 10, a $C_5$-$C_{10}$-cycloalkyl radical optionally substituted, a (bis)methylenecycloalkylene radical of from 6 to 12 carbon atoms, or an o—, m— or p-phenylene radical optionally substituted, and k, l and q are each an integer from 1 to 80, and $A_k$ and $C_q$ alternatively are single bonds, and at least one of the radicals $A_k$, $B_l$, and $C_q$ contains two oxygen atoms, and Z is H, $C_1$-$C_6$-alkyl, phenyl, phenyl substituted by straight-chain or branched-chain $C_1$-$C_{20}$-alkyl, or a radical of the formula

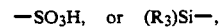

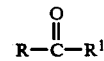

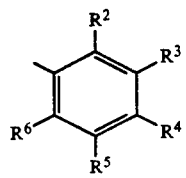

—$SO_3H$, or $(R_3)Si$—, or when R denotes an aryl radical, one of the radicals $R^2$ to $R^6$ is optionally a sulfur atom which links the aryl radical to $R^1$ in its ortho-position.

2. A compound containing carbonate groups and carbonyl groups, and having the general formula (I)

$$R-\overset{O}{\underset{\|}{C}}-R^1 \quad (I)$$

in which

R is a straight-chain $C_1$-$C_4$-alkyl radical, a branched-chain $C_3$-$C_4$-alkyl radical optionally substituted, a $C_6$-$C_{20}$-aryl radical, or a radical $R^1$, where $R^1$ has the following formula

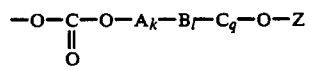

in which each of $R^2$ to $R^6$ is H, $C_1$-$C_4$-alkyl, phenyl, OH, $OCH_3$, $OC_2H_5$, SH, $SCH_3$, $SC_2H_5$, $SO_3H$, $SO_3^\ominus$, F, Cl, Br, or $CF_3$, provided that $R^2$ and $R^6$ are not OH, SH, or primary or secondary alkyl and at least one but not more than three of the radicals $R^2$ to $R^6$ is a radical of the formula $$-O-\underset{\underset{O}{\|}}{C}-O-A_k-B_l-C_q-O-Z$$

in which

A, B and C may be the same or different and each is a radical of the formula

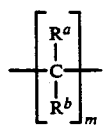

in which m is an integer from 1 to 6, and each of $R^a$ and $R^b$ is H, OH, aryl, $SO_3H$, or $C_1$-$C_4$-alkyl, a divalent oxaalkylene radical of the formula

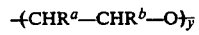

where y is an integer from 1 to 80 and $R^a$ and $R^b$ have the meanings stated, a radical of the formula

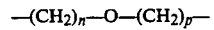

where n is an integer from 1 to 5 and p is an integer from 1 to 5, a polyoxaalkylene radical of from 2 to 20 oxygen atoms linked by at least one —$CH_2$— or —$CH_2$—$CH(CH_3)$-group, a $C_5$-$C_{10}$-cycloalkyl radical optionally substituted, a (bis)methylenecycloalkylene radical of from 6 to 12 carbon atoms, or an o—, m— or p-phenylene radical optionally substituted, and k, l and q are each an integer from 1 to 80, and $A_k$ and $C_q$ alternatively are single bonds, and at least one of the radicals $A_k$, $B_l$, and $C_q$ contains two oxygen atoms, and z is H, $C_1$-$C_6$-alkyl, phenyl, phenyl substituted by straight-chain or branched-chain $C_1$-$C_{20}$-alkyl, or a radical of the formula

or when R is an aryl radical, one of the radicals $R^2$ to $R^6$ is optionally a sulfur atom which links the aryl radical to $R^1$ in its ortho-position.

3. The compound

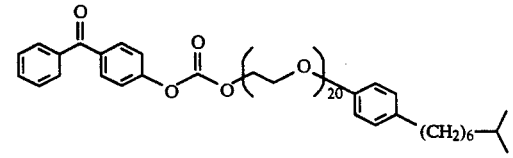

* * * * *